United States Patent
Harwood et al.

(10) Patent No.: US 7,160,307 B2
(45) Date of Patent: Jan. 9, 2007

(54) HIP REPLACEMENT INCISION LOCATOR

(75) Inventors: David Harwood, New Brunswick, NJ (US); Phillip Frederick, Memphis, TN (US); Russell Walter, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 221 days.

(21) Appl. No.: 10/775,561

(22) Filed: Feb. 10, 2004

(65) Prior Publication Data

US 2004/0220579 A1    Nov. 4, 2004

Related U.S. Application Data

(60) Provisional application No. 60/446,209, filed on Feb. 10, 2003.

(51) Int. Cl.
*A61B 17/58*    (2006.01)
(52) U.S. Cl. ....................................... 606/89
(58) Field of Classification Search .......... 606/87, 606/88, 89
See application file for complete search history.

(56) References Cited

U.S. PATENT DOCUMENTS

| | | | |
|---|---|---|---|
| 4,760,844 A * | 8/1988 | Kyle | 606/65 |
| 4,952,214 A * | 8/1990 | Comparetto | 606/87 |
| 5,843,085 A * | 12/1998 | Graser | 606/87 |
| 6,315,718 B1 * | 11/2001 | Sharratt | 600/228 |
| 6,551,325 B1 | 4/2003 | Neubauer et al. | |
| 2002/0099447 A1 | 7/2002 | Mears et al. | |
| 2002/0116067 A1 | 8/2002 | Mears et al. | |
| 2002/0161446 A1 | 10/2002 | Bryan et al. | |
| 2003/0004513 A1 | 1/2003 | Guzman et al. | |
| 2003/0051362 A1 | 3/2003 | Buckman et al. | |
| 2003/0158559 A1 | 8/2003 | Diaz | |
| 2003/0182815 A1 | 10/2003 | Carlson, II | |
| 2003/0187458 A1 | 10/2003 | Carlson, II | |

* cited by examiner

*Primary Examiner*—Corrine McDermott
*Assistant Examiner*—William H Matthews
(74) *Attorney, Agent, or Firm*—Kilpatrick Stockton LLP

(57) ABSTRACT

Methods and devices for performing hip replacement surgery are described. According to one embodiment, a method comprising providing an incision locator comprising a first wing and a second wing, the first wing adapted to be oriented generally along the femoral axis of a femur forming the hip on which the surgery is being conducted, positioning a proximal portion of the first wing adjacent to the greater trochanter, positioning other portions of first wing generally parallel to the femoral axis, indicating a proper placement of an incision based at least in part on the position of the second wing of the incision locator, performing an incision using at least one incision guide in at least one of the first and second wings, and completing the surgical procedure is described.

24 Claims, 3 Drawing Sheets ial patent application Ser. No. 60/446,209 filed on Feb. 10, 2003 entitled "Hip Replacement Incision Locator."

HIP REPLACEMENT INCISION LOCATOR

RELATED APPLICATION

The present application claims the benefit of provisional patent application Ser. No. 60/446,209 filed on Feb. 10, 2003 entitled "Hip Replacement Incision Locator."

FIELD OF THE INVENTION

The invention relates generally to devices for ensuring proper location for incision in hip replacement surgery and their methods of use.

BACKGROUND OF THE INVENTION

When beginning a hip replacement surgery, it is important for the surgeon to make the initial incision at the correct location. Incorrect placement or alignment of incisions can result in lengthening the incision, a greater loss of blood, and lengthened recovery times. To reduce the occurrence of incorrect incision placement, surgeons use diverse methods in their attempts to ascertain the internal placement of bones and joints, and thus the correct location for incision.

Some surgeons palpate the hip of a patient in order to find landmarks which correspond with internal structures. Others use rulers, protractors, or other methods of measurement in an attempt to get as close as possible to the correct location. Still others may only extrapolate from past experiences and patients in their determination of the correct incision location.

These methods, however, can present obvious difficulties and disadvantages. Educated guesses, even made by surgeons with a long line of past experience, can result in incorrect placement. Devices and methods are therefore needed for ensuring proper placement of the initial incision in a total hip replacement surgery which is both accurate and reproducible.

SUMMARY OF THE INVENTION

Various embodiments of the present invention provide locators for proper placement of the initial incision when performing a total hip replacement surgery. According to one embodiment of the present invention, the incision locator is "V" shaped, having a first wing and a second wing which extend from a common point. According to other embodiments, the incision locator is any geometric shape in which placement of one portion along or in a known relationship to the femoral axis determines the proper location of incision.

According to one aspect of the present invention, the incision locator is a one-piece design. In other embodiments, the incision locator can be formed from separate components.

According to certain embodiments of the present invention, the first wing is adapted to be oriented generally along the femoral axis of a patient during hip replacement surgery. The position of the second wing is then used to generally identify the proper location and placement of the incision.

In certain embodiments of the present invention, the proper location of the first wing of the incision locator is determined through palpation of the patients greater trochanter. In other embodiments, measurements are taken along the femoral axis to determine proper location. In still other embodiments, proper placement of the first wing is accomplished through the use of fluoroscopy.

In certain embodiments of the present invention, the angle formed by the first and second wings of the incision locator is approximately 30 degrees. In other embodiments, the angle is adjustable to account for differences in patient body shape.

Another embodiment of the present invention includes a method of locating the proper incision point in a hip replacement surgery through the use of devices described herein. In certain embodiments, a surgeon palpates a patient's hip to locate the greater trochanter and center of the femur, positions a proximal portion of the first wing adjacent to the greater trochanter, positions other portions of first wing generally parallel to the femoral axis, and locates a proper placement of an incision based at least in part on the position of the second wing of the incision locator.

In certain embodiments, lines or markings are drawn on the patient's skin indicating the femoral axis and the tip of the greater trochanter. In other embodiments, pins are used to mark the desired locations. The incisions may be made simply using devices according to various embodiments of the invention as a cutting guide. Any other components and techniques can be used to show where the incision or incisions should be made.

In a certain embodiments of the present invention, the incision locater is used in conjunction with fluoroscopy, so that a surgeon or surgical assistant can locate the femoral axis and greater trochanter with precision. This embodiment of the present invention is especially useful where patient figure or other factors make palpation difficult, or when a more accurate internal alignment is needed.

Another embodiment of the present invention includes methods for performing hip replacement surgery through the use of the devices such as those described herein. In certain embodiments, a surgeon palpates a patient's hip to locate the greater trochanter and center of the femur, positions a proximal portion of the first wing adjacent to the greater trochanter, positions other portions of first wing generally parallel to the femoral axis, locates a proper placement of an incision based at least in part on the position of the second wing of the incision locator, makes an incision using at least one incision guide in at least one of the first and second wings, and completes the surgical procedure.

DETAILED DESCRITPION

Figure 1:
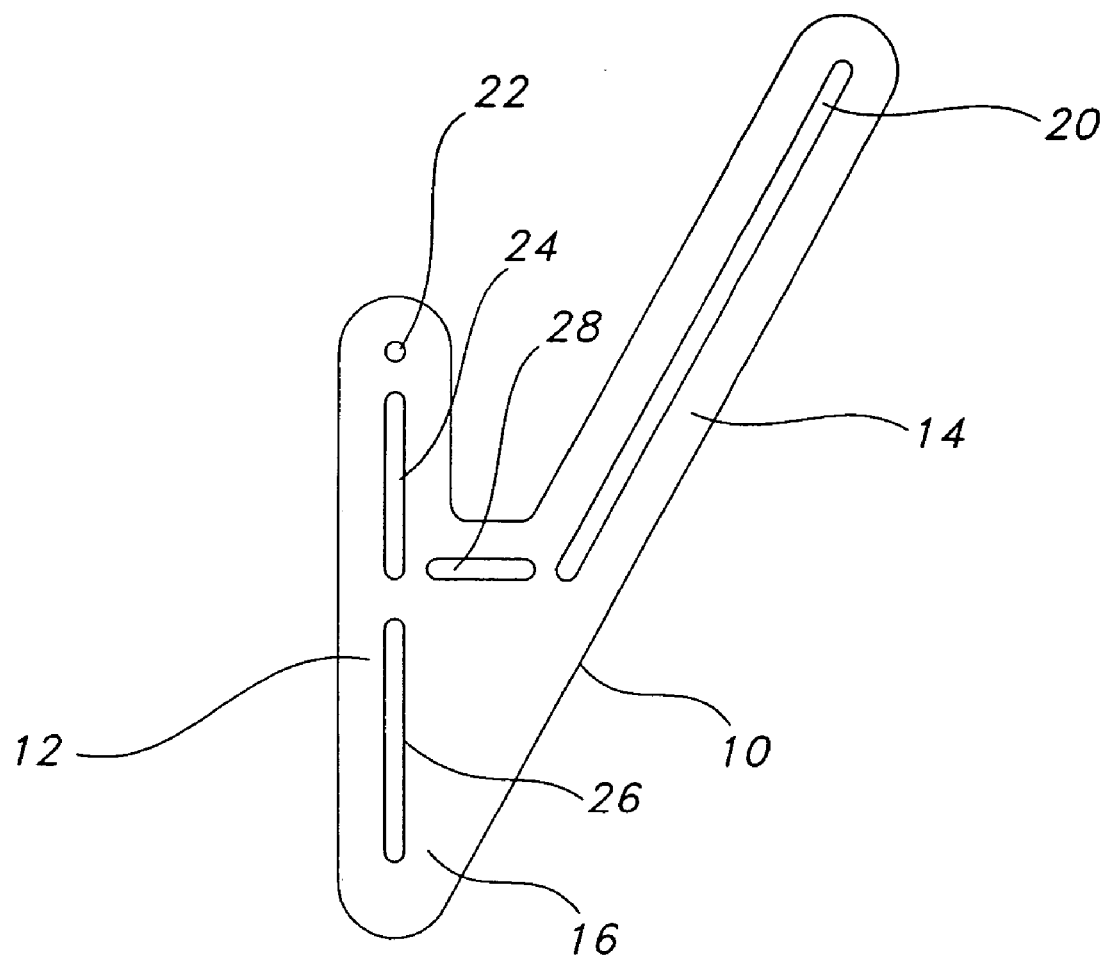
FIG. 1 illustrates a device according to one embodiment of the present invention.

Methods and devices according to certain embodiments of the present invention assist a surgeon to determine a proper initial incision when performing a total hip replacement surgery. FIG. 1 shows a device according to one embodiment of the present invention comprising an incision locator 10. According to certain aspects of some embodiments of the present invention, the incision locator 10 comprises a first wing 12, a second wing 14, and a connecting portion 16. Alternatively, the first and second wing may comprise portions of an integral geometric shape such as a triangle, quadrilateral, or other suitable shape. According to aspects of certain embodiments, the second wing forms an angle with the first wing. According to certain embodiments, the angle can be substantially a thirty degree angle. According to aspects of other embodiments, the first wing and second wing may be attached at a pivoting point allowing a variety of angles to be selected in order to accommodate differences in patient physique.

According to aspects of the embodiment depicted in FIG. 1, the first wing 12 comprises a first incision locator 22, a second incision locator 24, and a third incision locator 26. In use, the incision locators can be used to assist a surgeon in orienting the incision locator 10 with anatomical features. According to aspects of other embodiments, fewer incision locators may be used or more incision locators may be used.

According to the embodiment depicted in FIG. 1, the second wing 14 comprises an incision locator 20. According to certain aspects of the embodiment depicted in FIG. 1, the incision locator 20 of the second wing 14 is ten centimeters in length. In use, the incision locator 20 can be used by a surgeon to determine a proper incision for a hip replacement surgery.

Figure 2:
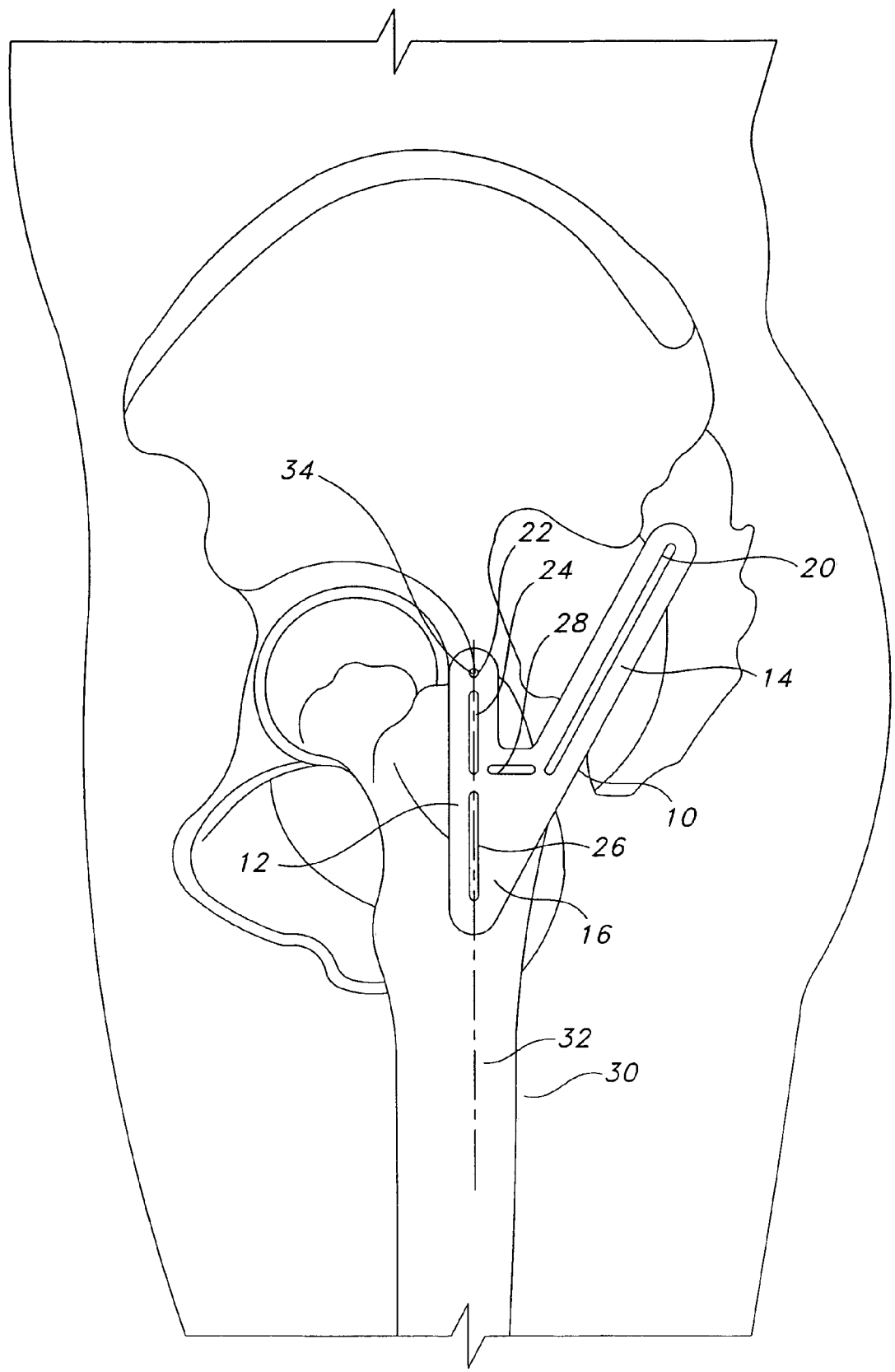
FIG. 2 illustrates the device of FIG. 1 positioned in proper alignment to determine an incision point for a hip replacement surgery.

According to the certain aspects of the embodiment depicted in FIG. 2, the incision locator 20 can determine a proper incision for a posterior approach in a hip replacement surgery. Other suitable approaches may be determined according to other aspects of embodiments of the present invention. According to aspects of other embodiments, the incision locator 20 of the second wing 14 can be any other suitable length as determined by clinical experience, clinical trials, or other appropriate method.

According to the embodiment depicted in FIG. 1, the connecting portion 16 is substantially triangular in shape, or, alternatively, another suitable shape. According to other embodiments, the connecting portion could comprises a portion of an integral geometric shape which can comprise the first wing 12 and the second wing 14. The connecting portion 16, according to the embodiment depicted in FIG. 1, further comprises an incision guide 28. In the embodiment depicted in FIG. 1, the incision guide 28 is substantially perpendicular to the first, second, and third incision locators 22, 24, and 26 of the first wing 12.

FIG. 2 illustrates a lateral view of a patient's leg with the incision locator 10 in place. The patient's leg illustrated in FIG. 2 comprises a femur 30, a femoral axis 32, and a greater trochanter of the center femur 34. For illustration purposes, methods in accordance with the present invention will be explained in connection with FIG. 2. To determine a proper placement of an incision for a hip replacement surgery, a surgeon, or other suitable person, can palpate a patient's leg and locate the tip of the greater trochanter 34. According to certain embodiments, the surgeon can mark the location of the tip of the greater trochanter 34 with a marking device such as a pin, skin marking, or other suitable method.

Once the position of the tip of the greater trochanter 34 is determined, the surgeon can determine the position of the center of the femur and make a marking, such as a line on the surface of the patient's leg, indicating the femoral axis 32. According to other embodiments of the present invention, the surgeon may use fluoroscopy, magnetic resonance imaging, anatomical measurements, or other suitable imaging or measuring techniques in addition to, or in place of, palpation to determine proper placement of the incision locator 10, and/or the position of the tip of the greater trochanter 34, and/or the position of the femoral axis 32.

Once the surgeon determines and indicates the position of the tip of the greater trochanter 34 and the femoral axis 32 by palpation, measuring, imaging, or other suitable method, the incision locator is placed on the patient's leg in the area of the greater trochanter 34. According to the embodiment depicted in FIG. 2, the first wing 12 is placed in the area of the femoral axis 32 and the second wing 14 is pointed posteriorly. The surgeon then aligns one or more of the incision guides with the tip of the greater trochanter 34. According to aspects of the embodiment depicted in FIG. 2 for illustration purposes, the first incision guide 22 of the first wing 12 is aligned with the tip of the greater trochanter 34 using the pin or other suitable marking used to indicated the location of the tip of the greater trochanter 34.

After aligning the tip of the greater trochanter with the first incision guide 22, according to aspects of the embodiment depicted in FIG. 2, the surgeon then aligns the femoral axis 32 with the second and third incision guides 24 and 26 of the first wing 12. With the incision locator 10 on the patient's leg, the first incision guide aligned with the tip of the greater trochanter 34, and the second and third incision guides aligned with the femoral axis 32, the incision guide 20 of the second wing 14 of the incision locator 10 indicates a proper placement of an incision. According to the embodiment shown in FIG. 2, the incision guide 20 indicates a proper position for a ten centimeter incision for a posterior approach for a hip replacement procedure.

Figure 3:
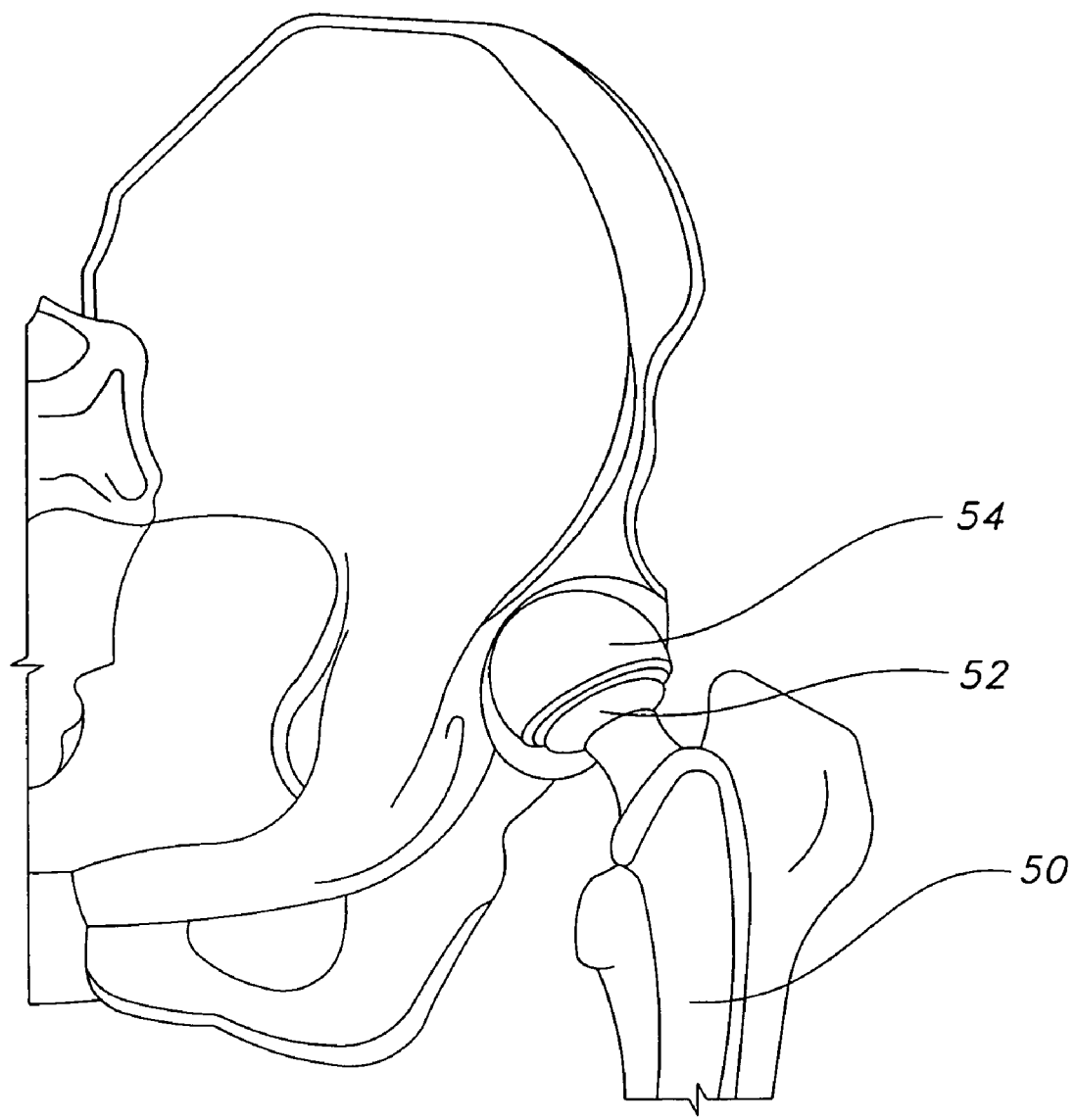
FIG. 3 illustrates aspects of hip replacement surgery conducted with devices and methods according to certain embodiments of the invention.

With the incision locator 10 in place, the surgeon can either mark the placement of the incision through the incision guide 20, remove the incision locator 10, and proceed to make an incision along the mark indicating the placement of the incision, or alternatively, the surgeon can make the incision with the incision locator 10 in place, using the incision guide 20 to guide the cutting instrument. Once the incision is performed, the surgeon proceeds to perform a hip replacement procedure according to standard surgical procedure, including placing and installing, using conventional procedures, components such as a femoral hip replacement component 50, a femoral stem 52, and an acetabular cup 54 as illustrated in FIG. 3.

The foregoing has been provided for purposes of disclosure of preferred embodiments of the invention. Changes, additions, omissions may be made to the devices and processes disclosed in this document without departing from the scope or spirit of the invention.

What is claimed is:

1. A method for conducting hip replacement surgery, comprising:
   providing an incision locator comprising a first wing and a second wing, the first wing adapted to be oriented generally along a femoral axis of a femur forming a hip on which surgery is being conducted;
   positioning a proximal portion of the first wing adjacent to a tip of a greater trochanter;
   positioning other portions of first wing generally parallel to the femoral axis;
   indicating a proper placement of an incision based at least in part on the position of the second wing of the incision locator;
   performing an incision using at least one incision guide in at least one of the first and second wings; and
   completing the surgical procedure.

2. The method of claim 1, wherein the incision is a ten centimeter incision for a posterior approach in a hip replacement procedure.

3. The method of claim 1, wherein an angle between the first and second wing is substantially a 30 degree angle.

4. The method of claim 1, wherein an angle between the first and second wing can be selectively adjusted.

5. The method of claim 1, wherein the first and second wing are portions of an integral geometric shape.

6. The method of claim 5, wherein the integral geometric shape is a triangle.

7. The method of claim 1, wherein at least one of the incision guides is an opening in a surface of the incision locator.

8. The method of claim 1, wherein the incision is performed using at least one incision guide of the second wing.

9. The method of claim 1, wherein the incision is performed using at least one incision guide of the first wing.

10. The method of claim 1, wherein the incision is performed using at least one incision guide of both the first and the second wing.

11. A method comprising:
    providing an incision locator comprising a first wing and a second wing, the first wing comprising at least a first incision guide and a second incision guide and the second wing comprising at least one marking opening;
    providing an indication of a femoral axis on a patients leg;
    providing an indication of a greater trochanter tip on a patients leg;
    aligning the first incision guide with the indication of the greater trochanter tip;
    aligning the second incision guide with the indication of the femoral axis;
    aligning the second wing of the incision guide to point posteriorly; and making an incision based at least in part on the incision guide of the second wing.

12. The method of claim 11, wherein the incision is a ten centimeter incision for a posterior approach in a hip replacement procedure.

13. The method of claim 11, wherein providing an indication of a greater trochanter tip comprises placing a pin on the surface of patient's leg.

14. The method of claim 11, wherein palpation is used to assist in aligning the incision locator.

15. The method of claim 11, wherein fluoroscopic images are used to assist in aligning the incision locator.

16. The method of claim 11, wherein anatomical measurements are used to assist in aligning the incision locator.

17. The method of claim 11, wherein an angle between the first and second wing is substantially a 30 degree angle.

18. The method of claim 11, wherein an angle between the first and second wing con be selectively adjusted.

19. The method of claim 11, wherein the first and second wing are portions of an integral geometric shape.

20. The method of claim 19, wherein the integral geometric shape is a triangle.

21. The method of claim 11, wherein at least one of the incision guides is an opening in a surface of the incision locator.

22. The method of claim 11, wherein the incision is performed using at least one incision guide of the second wing.

23. The method of claim 11, wherein the incision is performed using at least one incision guide of the first wing.

24. The method of claim 11, wherein the incision is performed using at least one incision guide of both the first and the second wing.

* * * * *